(12) United States Patent
Joachim et al.

(10) Patent No.: US 6,379,700 B2
(45) Date of Patent: Apr. 30, 2002

(54) PROCESS FOR MANUFACTURING TABLETS FOR THE SUSTAINED RELEASE OF ACTIVE PRINCIPLE(S)

(75) Inventors: Joseph Joachim, Marseilles; Pascal Prindirre, Chateaurenard; Nabil Farah, Lyons, all of (FR)

(73) Assignees: Gattefosse S.A., Saint Priest; Ethypharm, Houdan, both of (FR)

( * ) Notice: Subject to any disclaimer, the term of this patent is extended or adjusted under 35 U.S.C. 154(b) by 0 days.

(21) Appl. No.: 09/733,668

(22) Filed: Dec. 8, 2000

Related U.S. Application Data

(63) Continuation of application No. PCT/FR99/01443, filed on Jun. 16, 1999.

(51) Int. Cl.$^7$ .................................................. A61K 9/22
(52) U.S. Cl. ........................ 424/468; 424/470; 424/465; 514/784; 514/785
(58) Field of Search ................................ 424/468, 470, 424/465, 489

(56) References Cited

U.S. PATENT DOCUMENTS

| | | | |
|---|---|---|---|
| 4,199,560 A | 4/1980 | Gyarmati et al. ............. 424/19 |
| 4,684,632 A | * 8/1987 | Schulz et al. ................. 514/78 |

FOREIGN PATENT DOCUMENTS

| | | |
|---|---|---|
| JP | 8-198776 | 6/1996 |
| WO | 87/04070 | 7/1987 |
| WO | 94/06416 | 3/1994 |
| WO | 94/12180 | 6/1994 |
| WO | 98/14176 | 4/1998 |

OTHER PUBLICATIONS

Gyarmati et al. "Solid oral pharmaceutical compositions of regulated rate of release" *Chem. Abstracts*, 83, No. 20 (1975).
Zelko et al. "Effect of the starting material on the dissolution characteristics . . . " *Pharm. Sci.* 2, 169–171 (1996).
Prinderre et al. "Evaluation of Some Protective Agents on Stability and Controlled . . . " *Drug. Dev. Indus. Pharm.* 23, 817–826 (1997).
Walia et al. "Preliminary Evaluation of an Aqueous Wax Emulsion for Controlled–Release Coating" *Pharm. Dev. Tech.* 3, 103–113 (1998).

* cited by examiner

Primary Examiner—James M. Spear
(74) Attorney, Agent, or Firm—Heslin Rothenberg Farley & Mesiti P.C.

(57) ABSTRACT

The invention concerns a method for making tablets with active principle sustained-release which consists in: preparing a fluid oil-in-water emulsion; spraying the resulting emulsion on a powder mixture containing at least the active principle; subjecting said treated powder to a compressing step, to obtain tablets.

12 Claims, 7 Drawing Sheets

PROCESS FOR MANUFACTURING TABLETS FOR THE SUSTAINED RELEASE OF ACTIVE PRINCIPLE(S)

CROSS REFERENCE TO RELATED APPLICATIONS

This application is a continuation of PCT application PCT/FR99/01443 filed Jun. 16, 1999, which claimed the priority of French application FR/98.07725, filed Jun. 16, 1998. The entire disclosures of both are incorporated herein by reference.

The invention relates to a process for manufacturing tablets for the sustained release of active principle(s), as well as to the tablets thus obtained.

In the description and in the claims, the expression "tablet for the sustained release of an active principle" denotes a tablet which can extend the therapeutic effect of the active principle in tissues or in the blood over a sustained period of time (see in particular "The Science and Practice of Pharmacy", 19th edition, Remington 1975).

Several processes have been proposed for manufacturing tablets of this type.

Thus, for example, documents, FR-A-2 417 982 and HU-A-9960 disclose a process for manufacturing delayed-action tablets by wet granulation. More specifically, the powder mixture comprising the active principle and the various adjuvants is blended with a granulation liquid consisting of an aqueous emulsion based on a hydrophobic component such as stearic acid and nonionic hydrophilic components such as polysorbates. The resulting wet mass is then dried, after which it is passed through a screen and the granules obtained are then pelletized so as to obtain tablets. The steps of blending, screening, drying and pelletizing the powder mixture make this process long and expensive.

Similarly, document WO 94/06416 discloses tablets consisting of a core coated with a double layer, respectively a first layer containing at least one immediate-release or modulated-release active principle, a second layer for the delayed release of active principle and an additional layer of low permeability. By means of a relatively long process, a tablet is thus obtained which has a complex structure and for which the release kinetics of the active principle are predetermined during manufacture.

Moreover, document WO 87/04070 discloses a process for spraying onto tablets an aqueous dispersion prepared by redissolving a dried lipid emulsion, based on wax or on hydrogenated oils, in water.

Document JP-A-53 062 821 discloses a process consisting in emulsifying a lipophilic substance melted in an aqueous phase and then in coating a pharmaceutical preparation by spraying with this emulsion at elevated temperature, above the melting point of the lipophilic substance (technique known as dry-spraying). Besides the fact that nothing is indicated regarding the nature of the coated pharmaceutical preparation, this technique has the drawback of resulting in, during spraying, an evaporation of the aqueous phase and thus in a modification of the coating conditions.

Document WO 98/14176 discloses a process for manufacturing tablets for the sustained release of active principle which are obtained by tableting granules that are hot-coated with a lipid matrix agent. This hot-coating technique not only has the drawback of giving rise to an additional energy expenditure, but also of requiring an adaptation of the standard equipment.

The problem which the invention proposes to solve is thus that of developing tablets for the sustained release of active principle(s) and whose manufacturing process is simple to carry out, potentially shorter and consequently less expensive than the processes proposed in the prior art.

To do this, the invention proposes a process for manufacturing tablets for the sustained release of active principles), in which:

an oil-in-water fluid emulsion is prepared;

the emulsion obtained is sprayed onto a powder mixture comprising at least the active principle;

the powder thus treated is subjected to a tableting step, in order to obtain tablets.

Specifically, it has been found, entirely surprisingly, that although the coated particles have no sustained-release properties, a subsequent conventional step of tableting these particles produces tablets that have sustained-release characteristics.

In one advantageous embodiment of the invention, the powder mixture comprises not only the active principle but also the formulation excipients.

The expression "formulation excipient" denotes the excipients required to formulate the desired presentation form.

Similarly, the tableting step can be carried out using any known excipient intended to promote the said tableting.

According to a first characteristic of the invention, the spraying-air temperature is between 20° C. and 60° C., advantageously 25° C., the temperature of the emulsion being set at between 20° C. and 25° C.

At a temperature above 60° C., the process becomes economically less viable. Moreover, a considerable risk of degradation of heat-sensitive active principles is noted.

In other words, besides the fact that this process makes it possible to obtain sustained-release tablets, it also has the advantage of being carried out at room temperature (the temperature of the spraying air and of the emulsion is advantageously equal to 25° C.) and is thus less expensive.

In one specific embodiment, the initial powder mixture is subjected beforehand to a granulation step in order to obtain granules.

To facilitate the spraying of the emulsion onto the powder mixture, the said emulsion is advantageously prepared by phase inversion, so as to modify the particle size distribution, thus making it possible to reduce the particle size and hence the viscosity of the emulsion.

According to another important characteristic of the invention, the oil-in-water fluid emulsion comprises from 5% to 35% by weight of fatty substance.

For a concentration of less than 5%, the concentration of fatty substance is insufficient to ensure sustained release of the active principle.

For a concentration of more than 35%, the viscosity is too high to obtain a fluid emulsion. In addition, the tableting step is difficult.

Moreover, to allow tableting of the particles, the said particles are coated in a proportion of from 3% to 100% by weight with fluid emulsion, advantageously from 10% to 60%.

For a coating of less than 3%, only partial coating of the particles is observed.

Similarly, for a coating of greater than 100%, the tablet becomes too big to be a suitable presentation form.

In order to obtain a sustained release of the active principle, the fatty substances are chosen from the group comprising fatty acids, hydrogenated oils, fatty acid esters of glycerol or of polyols, and natural waxes.

According to a first embodiment, the fatty substance chosen is glyceryl behenate sold by the Applicant under the trade name Compritol® 888 Ato.

According to another embodiment of the invention, the fatty substance is glyceryl palmitostearate sold by the Applicant under the trade name Precirol® Ato 5.

To prepare the fluid emulsion at room temperature, the emulsion also contains an emulsifier or surfactant.

The surfactant used is chosen from nonionic and/or ionic surfactants.

More specifically, the emulsifier will be chosen so as to make the emulsion fluid and stable and to ensure the absence of formation of a foam. In addition, the emulsifier must be pharmaceutically acceptable.

The emulsifier advantageously chosen is polyethylene glycol 4000 palmitostearate.

According to another embodiment, the emulsifier is sodium lauryl sulfate used in a proportion of from 0.5% to 1% relative to the weight of the emulsion. Beyond 1%, no improvement of the emulsion is obtained and the formation of a foam is observed.

Similarly, so as not to obstruct the tubes and nozzle of the spraying machine, the viscosity of the oil-in-water fluid emulsion is set at between 10 and 70 centipoises.

The invention also relates to the tablet for the sustained release of active principle(s) which can be obtained by the process described hereinabove.

The invention and the advantages arising therefrom will emerge more clearly from the implementation examples which follow, in support of the attached figures, in which:

In Examples 1 and 2 below, tablets whose active principle dissolution kinetics are said to be zero-order were manufactured according to the process of the invention.

Figure 1:
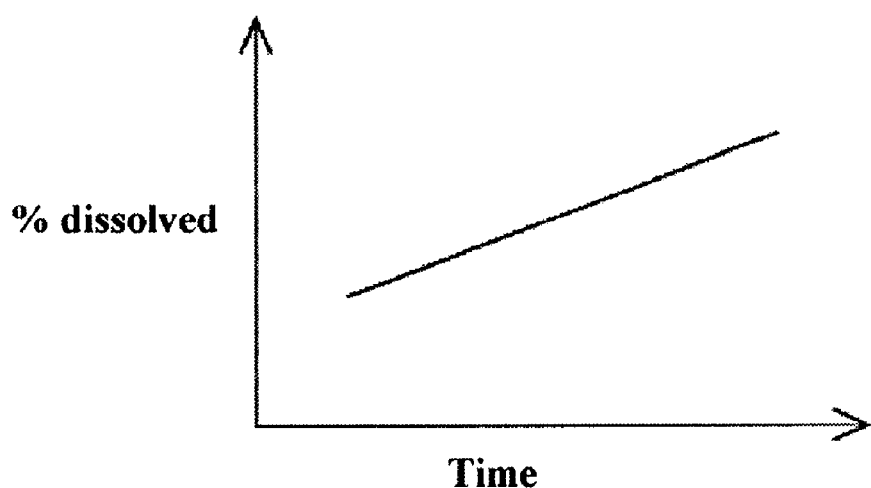
FIG. 1 is a representation of the release profile of a tablet having zero-order kinetics for dissolution of the active principle.

The expression "zero-order dissolution kinetics" denotes the constant and uniform release of the active principle as a function of time. This release may be represented graphically in the form of a curve expressed by the following equation:

$$dQ/dt = k$$

where Q corresponds to the amount of solution and k is the rate constant (see FIG. 1).

Figure 2:
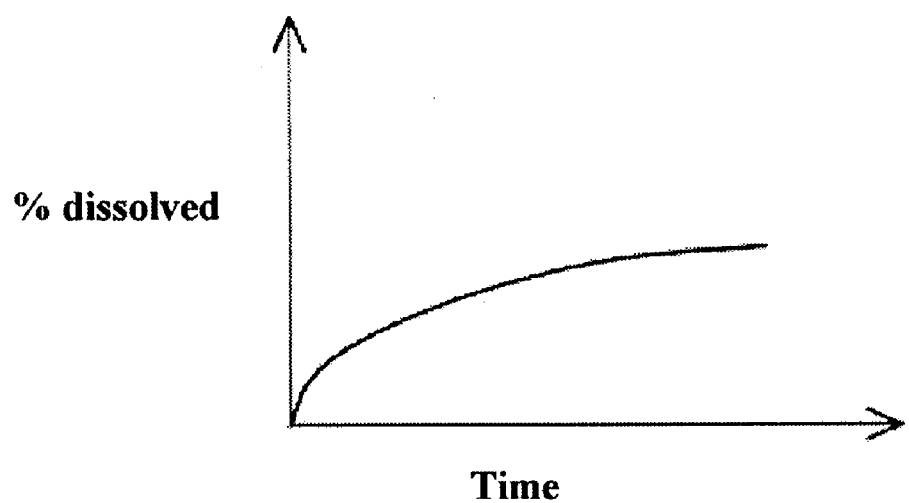
FIG. 2 is a representation of the release profile of a tablet having first-order kinetics for dissolution of the active principle.

Conversely, first-order kinetics correspond to a release proportional to the amount remaining in the presentation form envisaged and which decreases exponentially with time (see FIG. 2).

In Examples 1 and 2, the in-vitro release kinetics of the active principles are determined in a dissolumeter (conventional Sotax) in accordance with the European and US pharmacopeas, at pH 1.2. The spin speed of the paddles is 100 rpm.

EXAMPLE 1

This examples compares the release profile of theophylline granules coated according to the process of the invention before and after tableting with two different fatty substances, namely Compritol® 888 and Precirol® Ato 5, the spraying-air temperature being set at 25° C. or 60° C.

1—Preparation of the Granules

Granules corresponding to the formula below are prepared:

theophylline monohydrate: 30 grams lactose: 41 grams wheat starch: 16 grams sodium carboxymethylcellulose: 1 gram microcrystalline cellulose: 12 grams The granules are manufactured by wet granulation in a rotating-paddle Guedu mixer-granulator, carrying out the following steps:

prescreening of the theophylline monohydrate mixing together all the constituents in the mixer for three minutes;

blending for five minutes with 1500 ml of distilled water per five kilos of the initial mixture;

calibration of the semi-wet granules using a screen with a mesh size of 1.25 mm;

final oven-drying at 50° C.

2—Preparation of the Emulsion

A lipid emulsion is prepared comprising:

from 10% to 30% of fatty substance;

4% of stearate 4000 (surfactant);

remainder to 100% of distilled water. Compritol® 888 or Precirol® Ato 5 is used as fatty substance.

The fatty substance and the surfactant are heated until they have completely melted. The distilled water, heated to the same temperature, is added slowly with stirring. The addition of water gradually converts the initial water-in-oil emulsion into an oil-in-water emulsion. The emulsion is then homogenized with a Polytron homogenizer for three minutes in order to reduce and homogenize the size of the oil droplets.

However, when sodium lauryl sulfate is used as surfactant, it is dissolved hot in the aqueous phase.

3—Spraying of the Emulsion onto the Granules Previously Obtained

A machine with a flow of fluidized air is used, the fluidization-air temperature of which is set at 25° C. or 60° C. The fluidization pressure is set at about 1.5 bar. Similarly, the spraying rate is adjusted to 10 grams per minute.

Figure 3:
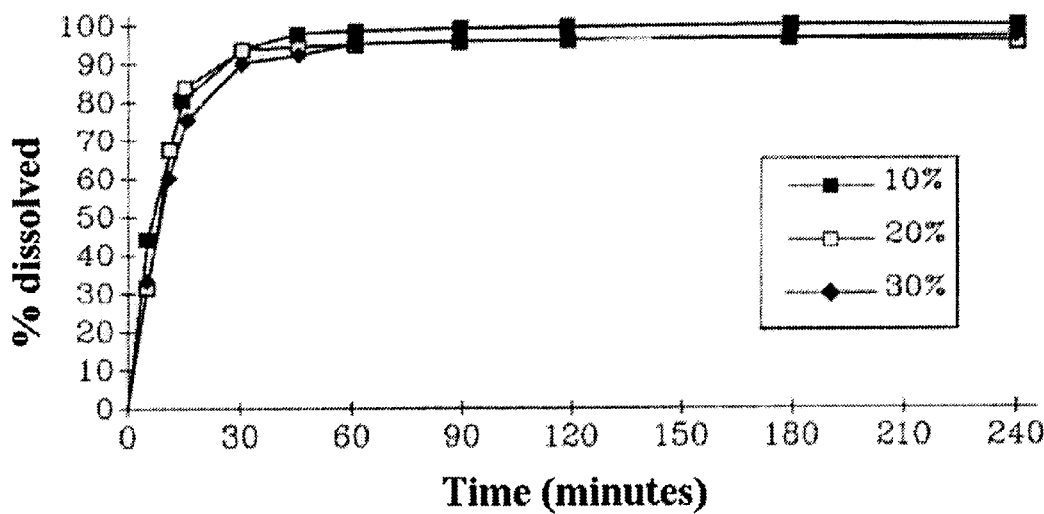
FIG. 3 represents the release profile of theophylline granules at a spraying-air temperature of 25° C. for the spraying of an emulsion based on Compritol® 888 Ato.
Figure 4:
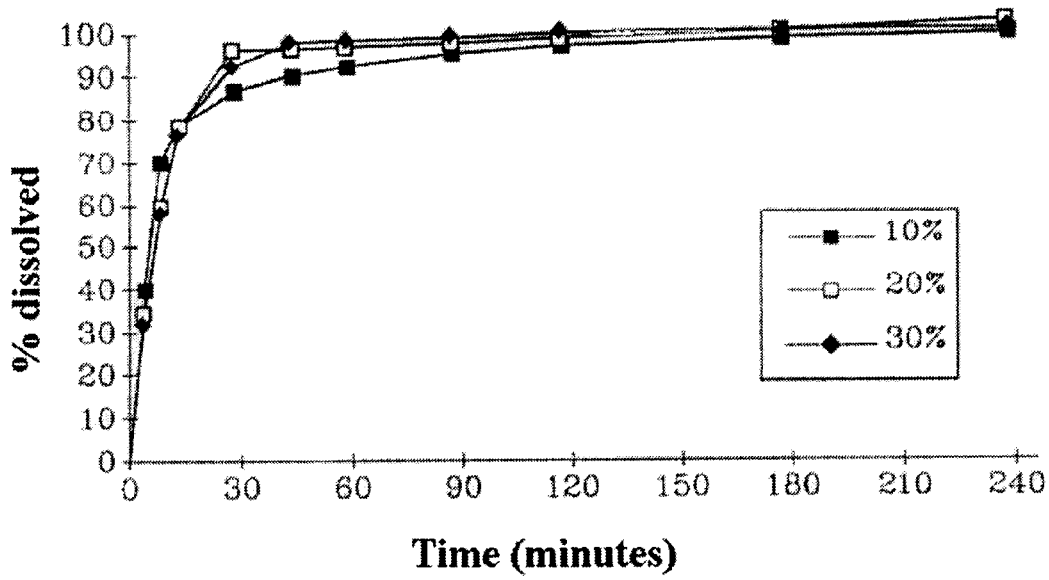
FIG. 4 represents the release profile of theophylline granules at a spraying-air temperature of 60° C. for the spraying of an emulsion based on Compritol® 888 Ato.

As already stated, the attached FIGS. 3 and 4 represent the release profile for theophylline granules coated with a lipid emulsion based on Compritol® 888 for spraying-air temperatures of 25° C. (FIG. 3) or 60° C. (FIG. 4). The proportion of Compritol® 888 ranges between 10% and 30% relative to the mass of solids used.

As these two figures show, irrespective of the spraying-air temperature, between 80% and 90% of the active principle is dissolved within thirty minutes of ingestion. It is concluded therefrom that the granules do not have sustained-release characteristics.

Figure 5:
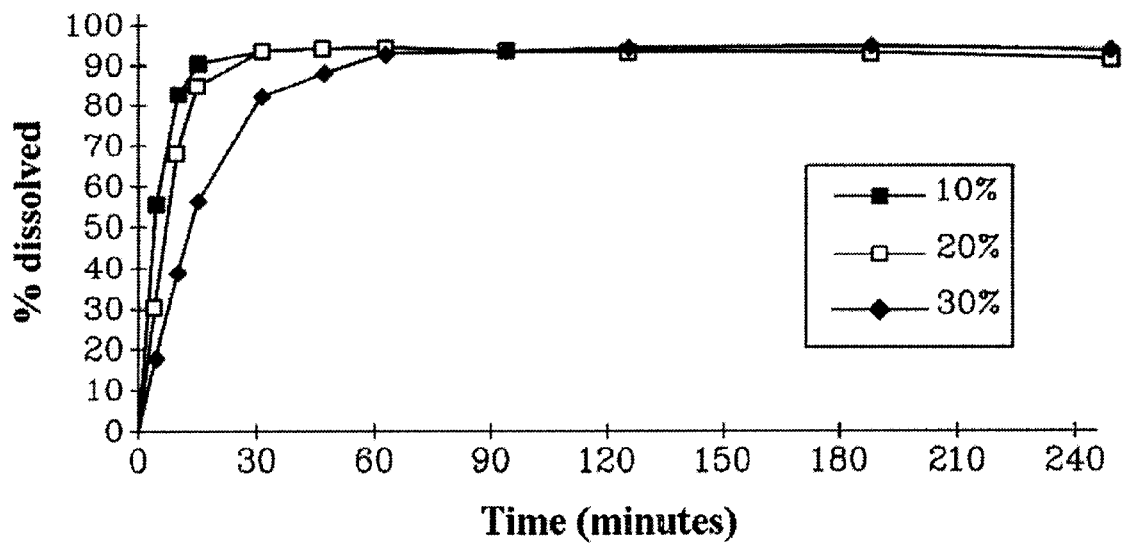
FIG. 5 represents the release profile of theophylline granules at a spraying-air temperature of 25° C. for the spraying of an emulsion based on Precirol® Ato 5.
Figure 6:
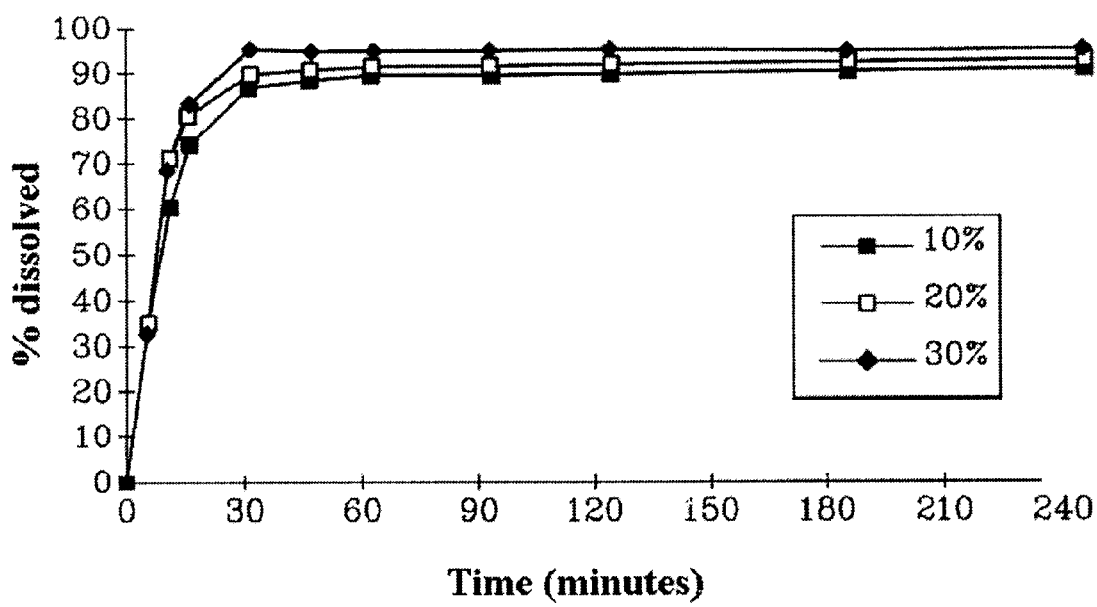
FIG. 6 represents the release profile of theophylline granules at a spraying-air temperature of 60° C. for the spraying of an emulsion based on Precirol® Ato 5.

FIGS. 5 and 6 represent immediate-release profiles when the emulsion used is based on Precirol® Ato 5.

As previously, it is found that between 80% and 95% of the active principle contained in the coated granules is released within thirty minutes.

4—Tableting Step

The granules coated with Compritol® are then subjected to a step of tableting using a Frogerais OA alternating tableting machine having punches of reference size D10-R10. A mixture of talc and magnesium stearate, each representing 1% by weight relative to the total weight of the granules, is used as tableting excipient. The tablets obtained have an average weight of 402 mg and an average hardness of 5.7 kg.

Figure 7:
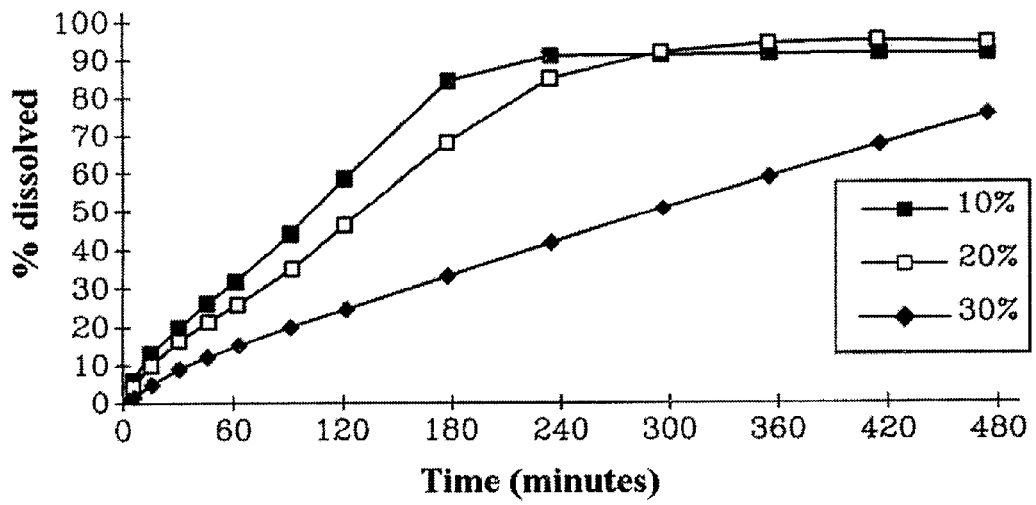
FIG. 7 represents the release profile of theophylline tablets at a spraying-air temperature of 25° C. for the spraying of an emulsion based on Compritol® 888 Ato.
Figure 8:
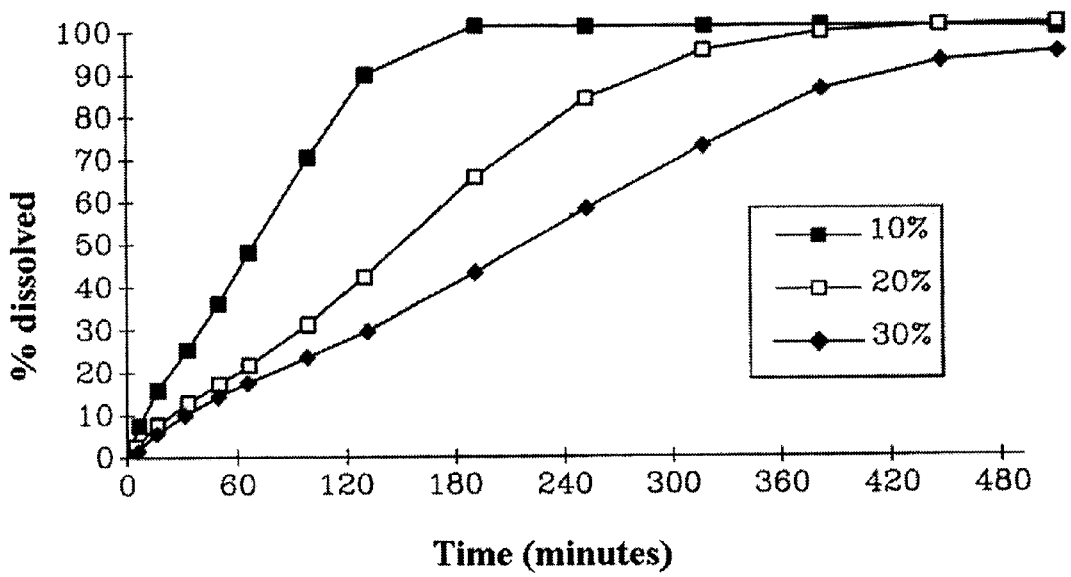
FIG. 8 represents the release profile of theophylline tablets at a spraying-air temperature of 60° C. for the spraying of an emulsion based on Compritol® 888 Ato.

As FIGS. 7 and 8 show, the tablets obtained from the granules manufactured at a spraying temperature of 25° C. (FIG. 7) or of 60° C. (FIG. 8) show zero-order kinetics for a Compritol® concentration in the emulsion of 30%.

Moreover, the process of the invention has the advantage of being able to be carried out at a spraying-air temperature of about only 25° C., which not only facilitates the various operations but also reduces the manufacturing cost, in particular in terms of energy consumed.

EXAMPLE 2—Diclofenac Tablets

1—Preparation of the Granules

Diclofenac particles are prepared under the same conditions as those of Example 1, starting with a Diclofenac/dicalcium phosphate mixture in proportions of 50/50.

2 and 3—Preparation of the Emulsion and Spraying

The granules are then coated with an emulsion under the same conditions as those of Example 1, at a spraying-air temperature of 25° C., while varying the nature and concentration of the lipid substance used. A proportion of 20% or 30% of Precirol® Ato or 30% of Compritol®, relative to the mass of solids used, is thus employed. 4—Tableting Step The step of tableting the coated granules is carried out on the same tableting machine as previously. The tableting characteristics and the characteristics of the tablets obtained are collated in this table below.

|  | Batch Compritol 30% | Batch Precirol 20% | Batch Precirol Ato 5 30% |
|---|---|---|---|
| Coated particle: | 91.4% | 92% | 91.4% |
| Encompress | 5.6% | 6% | 5.1% |
| Talc | 2% | 1% | 0.5% |
| Magnesium stearate | 0.5% | 1% | 1% |
| Silicone talc | 0.5% | 0% | 2% |
| Weight of the tablet | 350 mg | 300 mg | 350 mg |
| Hardness | 3 kg | 6 kg | 3 kg |
| Friability | 0.2% | 0.26% | 0.30% |

Figure 9:
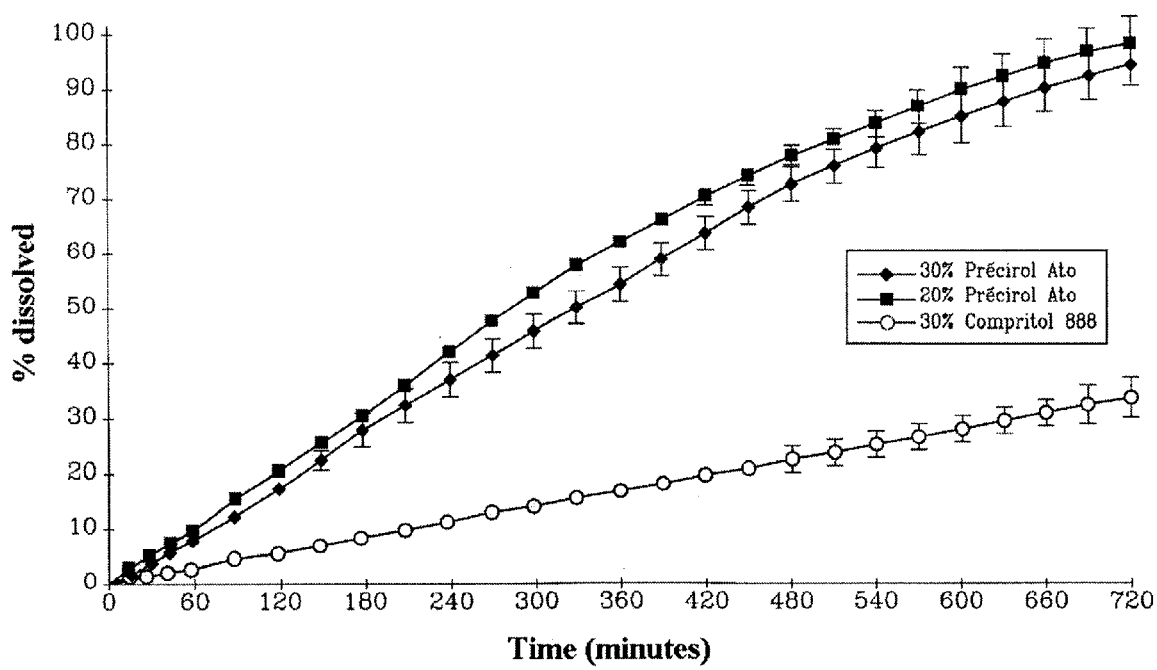
FIG. 9 represents the release profile of Diclofenac tablets manufactured from an emulsion based on Compritol® 888 Ato or Precirol® Ato 5 at a spraying temperature of 25° C.

As shown in FIG. 9, zero-order kinetics are obtained in the three cases.

Figure 10:
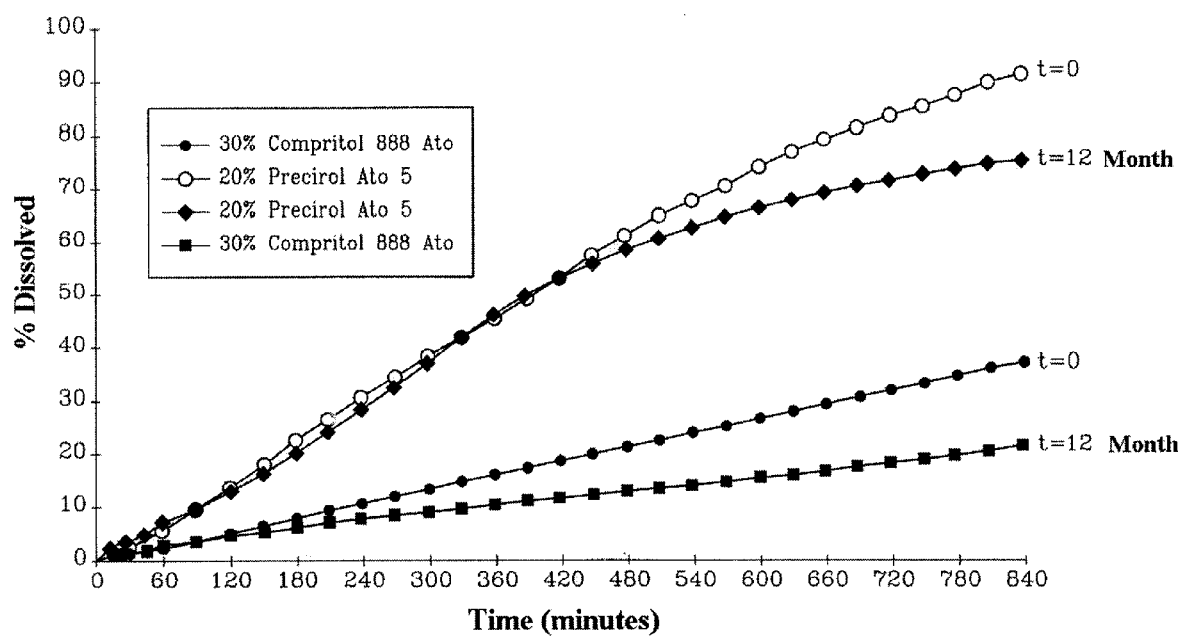
FIG. 10 represents the release profile of the same batch of Diclofenac tablets manufactured from an emulsion based on Compritol® 888 Ato or Precirol® Ato 5 before and after stability at 40° C.

Finally, FIG. 10 represents the release profiles of Diclofenac tablets coated with lipid emulsions comprising 20% of Compritol® 888 Ato or 20% of Precirol® Ato 5, before and after twelve months of stability at 40° C. and 75% relative humidity (accelerated stability).

It is found that the active principle remains stable and that a very satisfactory stability of the dissolution kinetics for the Diclofenac tablets is conserved.

EXAMPLE 3—Diclofenac Tablets

In contrast with Example 2, no prior wet granulation of the active principle is carried out in this example.

1—Preparation of the Fluid Emulsion

A fluid emulsion is prepared containing 10% of identical fatty substance under the same conditions as those used in Examples 1 and 2.

2—Spraying

The powder mixture consisting of a mixture of Diclofenac/dicalcium phosphate in proportions of 50/50 is then coated so as to obtain coated particles with good tableting properties.

The emulsion is sprayed onto the particles under the same conditions as those of Example 1, at a spraying-air temperature of about 25° C.

3—Tableting Step

The step of tableting the coated particles is carried out on an industrial rotary tableting machine. The tableting characteristics and the characteristics of the tablets obtained are as follows:

| | |
|---|---|
| Coated particle | 92% |
| Encompress | 6% |
| Talc | 1% |
| Magnesium stearate | 1% |
| Average weight of the tablet | 280 mg |
| Hardness | 33 Newtons |

Figure 11:
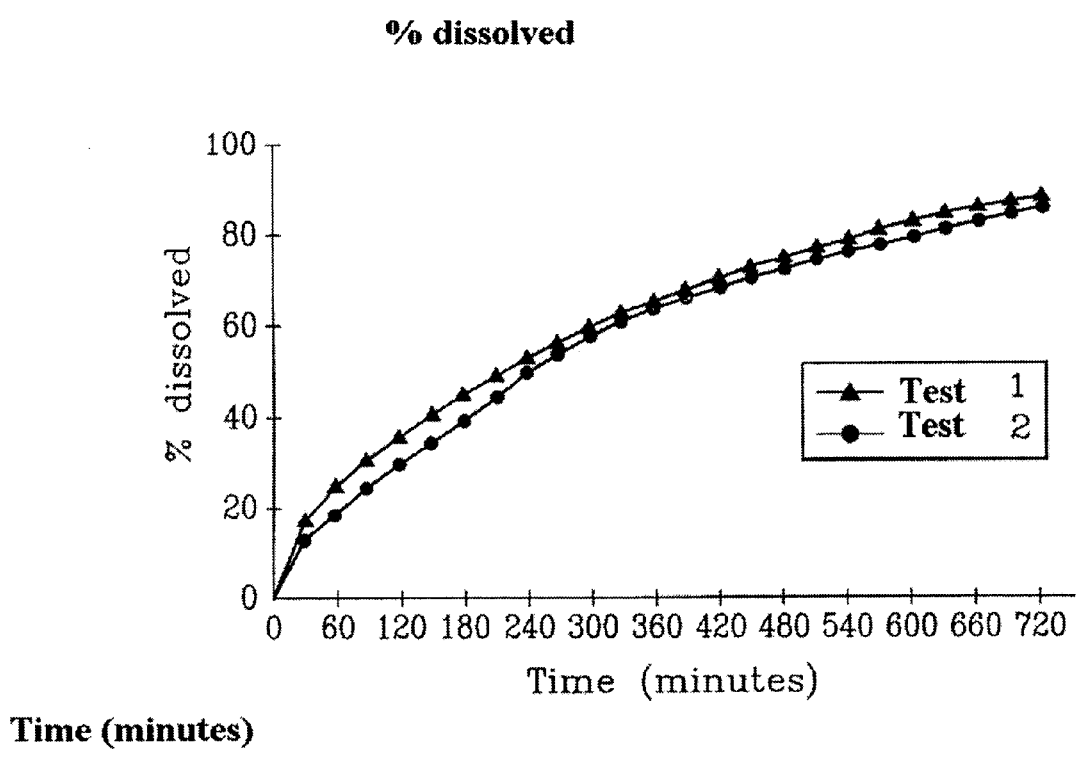
FIG. 11 represents the release profile of Diclofenac tablets manufactured from an emulsion based on Precirol® Ato 5 at a spraying-air temperature of 25° C.

FIG. 11 represents the release profile of Diclofenac tablets in which the proportion of Precirol® Ato 5 relative to the mass of solids used is 20%.

The in-vitro release kinetics of the Diclofenac are evaluated in a dissolumeter in accordance with the European, US and Japanese pharmacopeas, at pH 6.8, according to the provisions of US pharmacopea, edition XXIII. The spin speed of the paddles is 50 rpm.

As shown in FIG. 11, the two tests carried out on the same batch show a profile of sustained release of the active principle over 12 hours.

The advantages of the invention emerge clearly from the description.

It will be noted in particular that the process of the invention makes it possible to obtain tablets with sustained release over 12 hours, allowing the doses to be adapted to two intakes a day.

The ease of implementation of the process, consisting in spraying a lipid emulsion at temperatures ranging between 20° C. and 60° C., also contributing toward reducing the energy cost of the operations, will moreover be noted.

Finally, it is found that the tablets obtained have very satisfactory long-term stability.

What is claim is:

1. Process for the manufacture of tablets for the sustained release of active principle(s), in which:
    an oil-in-water fluid emulsion is prepared by phase inversion, said emulsion comprising an emulsifier, water and an oil phase consisting of one or more fatty substances chosen from the group consisting of fatty acids, hydrogenated oils, fatty acid esters of glycerol or polyols and natural waxes;
    the emulsion obtained is sprayed, at room temperature, onto a powder mixture comprising at least the active principle;
    the powder thus treated is subjected to a tableting step, in order to obtain tablets.

2. The process as claimed in claim 1, characterized in that the powder mixture is subjected beforehand to a granulation step.

3. The process as claimed in claim 1, characterized in that the spraying-air temperature is between 20° C. and 60° C.

4. The process as claimed in claim 1, characterized in that the oil-in-water fluid emulsion comprises from 5% to 35% by weight of fatty substance.

5. A sustained release tablet prepared according to the process of claim 1.

6. The process as claimed in claim 1, characterized in that the fatty substance is glyceryl behenate.

7. The process as claimed in claim 1, characterized in that the fatty substance is glyceryl palmitostearate.

8. The process as claimed in claim 1, characterized in that the emulsifier is chosen from the group consisting of non-ionic surfactants, ionic surfactants and mixtures of the two.

9. The process as claimed in claim 8, characterized in that the emulsifier is polyethylene glycol 4000 palmitostearate.

10. The process as claimed in claim 1, characterized in that the oil-in-water fluid emulsion has a viscosity of between 10 and 70 centipoises.

11. The process as claimed in claim 1, characterized in that the oil-in-water fluid emulsion is sprayed onto the powder mixture in a proportion of from 3% to 100% by weight relative to the weight of the powder mixture used.

12. A sustained release tablet according to claim 5 wherein (a) the powder mixture has been granulated; (b) the spraying is carried out at 20° C. to 60° C. with an amount of oil-in-water emulsion that constitutes from 3% to 100% of the weight of the powder; and (c) the oil-in water emulsion comprises a nonionic surfactant and from 5% to 35% by weight glyceryl behenate or glyceryl palmitostearate.

* * * * *